United States Patent [19]
Uelzmann

[11] 3,977,923
[45] Aug. 31, 1976

[54] METHOD AND SOLID PROPELLANT WITH UNSATURATED AZIRIDINE CURED BINDER

[75] Inventor: Heinz Uelzmann, Cuyahoga Falls, Ohio

[73] Assignee: The General Tire & Rubber Company, Akron, Ohio

[22] Filed: Dec. 3, 1969

[21] Appl. No.: 876,167

Related U.S. Application Data

[63] Continuation of Ser. No. 598,925, Dec. 5, 1966, abandoned, which is a continuation-in-part of Ser. No. 402,341, Oct. 7, 1964, abandoned.

[52] U.S. Cl.............................. 149/19.1; 149/19.5; 149/19.9; 149/19.91; 149/19.92
[51] Int. Cl.² ......................................... C06B 45/10
[58] Field of Search................. 149/19, 19.9, 19.92, 149/19.1, 19.91, 19.5; 260/85.1, 239 E, 78.4 R

[56] References Cited
UNITED STATES PATENTS

| | | | |
|---|---|---|---|
| 3,147,161 | 9/1964 | Abere et al............................ | 149/19 |
| 3,214,304 | 10/1965 | Vrieson................................. | 149/19 |
| 3,260,702 | 7/1966 | Murakami et al. ................. | 260/77.5 |
| 3,532,566 | 10/1970 | Lubowitz et al...................... | 149/19 |
| 3,883,375 | 5/1975 | Mastrolia et al................. | 149/19.91 |

OTHER PUBLICATIONS

Manecke et al., *Chemische Berichte*, 95 (11), 2700–2707, Nov. 1962.

*Primary Examiner*—Edward A. Miller
*Attorney, Agent, or Firm*—Kemon, Palmer & Estabrook

[57] ABSTRACT

A new class of multiaziridines are provided having the formula:

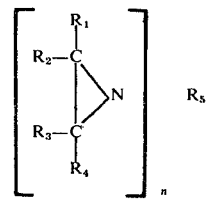

wherein
$R_1$, $R_2$, $R_3$ and $R_4$ are monovalent radicals that may be the same or different and are hydrogen, 1–5 carbon alkyl or 1–5 carbon alkenyl,
$R_5$ is a multivalent hydrocarbon radical containing 2 to 24 carbon atoms, and
$n$ is an integer from 2 to 4.

These multiaziridines are used to produce elastomeric compositions of controlled plasticity and gel content, plus other unique polymeric products, by reaction with polycarboxylic organic compounds, e.g., controlled combination of chain-extending and cross-linking of polycarboxylated polymers.

12 Claims, No Drawings

METHOD AND SOLID PROPELLANT WITH UNSATURATED AZIRIDINE CURED BINDER

CROSS-REFERENCE TO RELATED APPLICATION

This application is a continuation of Ser. No. 598,925, filed Dec. 5, 1966 (now abandoned) which in turn is a continuation-in-part of copending application Ser. No. 402,341, filed Oct. 7, 1964 (now abandoned).

BACKGROUND OF THE INVENTION

It is well known that polymeric materials which are thermoplastic and usually soluble in many organic solvents may be transformed by chemical reaction with suitable reagents into products of more complex chemical structure and higher molecular weight so they become non-thermoplastic, highly resistive to solvation by ordinary solvents or assume other new characteristics as a result of the chemical reaction. New polymeric products formed by such processes may acquire elastomeric qualities and their increased resistance to solution or attack by solvents is characterized by formation of gels when brought in contact with numerous solvents, this gelation being considered to constitute a measure of the extent of reaction of the initial polymeric material with the modifying agent.

Probably the most historic example of chemical reactions of this type involving polymer materials is the vulcanization of rubber with sulfur or sulfur producing reagents. In any event, this broad type of chemical reaction is referred to in the chemical arts by various terms dependent, at least to some extent, upon the degree or severity of reaction of the polymer material with the modifying agent. The terms "vulcanizing", "curing", "cross-linking" and "chain-extending" have been applied to this general form of operation and the modifying agents employed in such procedures are variously referred to as "curing agents", "vulcanizing agents", "cross-linking agents", "chain-extending agents" and other terms. For the purpose of the description of the present invention, the terms "curing" and "curing agent" will be employed for reference generally to this type of chemical reaction. In this context, the invention concerns curing of a specific class of polymeric materials which are known in the polymer art as carboxyl containing polymers. The curing agents are the new multiaziridines.

Where the "curing" is in the nature of chain extension, it is believed this takes place as a polyaddition with the formation of secondary amino groups. Where the "curing" is preliminarily in the nature of cross-linking, one explanation of the results of this invention is that secondary amino groups are known to react with ethylenimine rings much easier than with the propylenimine or butylenimine ring, forming, with ring-opening, substituted ethylene diamines. Secondary ammonium groups can be formed on the polymer chain by reaction of the —NH— groups with protons from the carboxyl groups present. Further reaction with ethylenimine di-adduct would then yield cross-linked polymer chains with the formation of ethylene diamine units.

Another possibility to account for the cross-linking reaction is a trimerization or oligomerization of the diaziridino-compound under the influence of protons from the dicarboxylic acid present. The resulting aziridine-trimers or oligomers subsequently can react with the dicarboxylic acid to form the cross-linked polymer.

Compounds which have been found useful as curing agents for polymer materials generally contain in their molecular structure a plurality of groups which can react with the molecules of the polymeric material in the curing, i.e., so-called "functional groups". The transformation of the polymer material into a more temperature and solvent resistant form is explained on the basis that polymer molecules are joined together by reaction with these functional groups into a three-dimensional network or, at the very least, a product of much greater molecular weight and complex structure. Accordingly, virtually all classes of compounds which possess a plurality of reactive or functional groups have been investigated as possible curing agents for a wide variety of polymer materials.

The aziridino group possesses a relatively high degree of reactivity and considerable attention has been devoted to the formation of various classes of compounds containing a plurality of aziridino groups. For example, the aziridino group may appear as a phosphoramide (U.S. Pat. No. 3,226,377), as an alkyl or alkylene aziridine (U.S. Pat. No. 3,231,563), as a substituent of an epoxy compound (U.S. Pat. No. 3,240,720), as a carbamate (U.S. Pat. No. 3,223,681) or as an aziridino substituted ether (U.S. Pat. No. 3,187,463). As indicated by the general structural formula given above, the present invention concerns aziridino compounds which contain a plurality of aziridino groups as substituents on a specific class of hydrocarbons.

The patents noted above disclose a variety of ways in which aziridino compounds may be prepared. It is contemplated that new compounds of this invention and other products which are useable in accordance with the invention in the curing of carboxyl containing polymers may be prepared in any suitable fashion known to the art. However, the preparation of hydrocarbon diaziridines from corresponding hydrocarbon dihalides by condensation with alkylenimines, either as the free alkylene imine or the corresponding alkali metal salts, in the presence of a scavenger, such as amines (see U.S. Pat. No. 3,197,463) may be advantageously used in producing multiaziridines for the invention. Some of the multiaziridines may also be produced by the addition of an alkylenimine, such as ethylenimine, to a vinyl aromatic compound, e.g., divinyl benzene, di-isopropenyl benzene, and the like, in presence of an alkali metal catalyst such as sodium, potassium, and the like.

Since diaziridines contain a plurality of reactive groups, they have been investigated for use as curing agents for various natural and synthetic polymeric materials. Their use in the modification of natural and synthetic fibers and in the tanning of hides and skins by recourse to their multifunctional groups has been previously disclosed, e.g., see U.S. Pat. No. 3,169,122. A variation of this concept is the use of diaziridines in the treating of fibers and textiles to crease-proof or dimensionally stabilize the textiles, e.g., see U.S. Pat. No. 3,165,375. In a broader sense, the general concept of using multiaziridino compounds as cross-linking agents for polymers containing active hydrogens or their equivalents to produce three-dimensional polymer networks, thereby providing solid materials of improved properties has been disclosed, e.g., see U.S. Pat. No. 3,162,618. The present invention concerns improvements in the field of multiaziridino compounds and in their use as curing agents for certain classes of polymers and the discovery that particular forms of multiaziridines when used as curing agents for carboxyl containing polymers provide improved characteristics in resulting cured products as compared with the curing of such polymers by procedures known heretofore. In this connection, polycarboxylic organic compounds have previously been cross-linked with polyaziridinyl phosphorous compounds to yield cross-linked resinous and rubber compositions. This procedure was found to involve serious problems because the phosphorous compounds employed were not stable and could not be obtained in a consistently pure form.

OBJECTS

A principal object of this invention is the provision of new methods for curing of carboxyl containing polymers. Further objects include the provision of:

1. New processes for producing elastomeric products by reaction of carboxyl containing polymers with a specific class of multiaziridines.
2. New forms of elastomeric materials derived from carboxyl containing polymers.
3. New processes for chain extending carboxyl containing polymers.
4. New multiaziridines which have been found particularly useful as curing agents for carboxyl containing polymers.
5. New rubbery copolymeric compositions which are useful in producing binders for solid rocket propellants, sealants and the like with involving problems of product instability.
6. New methods of creating rubbery copolymeric products of desired properties by controlled combination of polymer cross-linking and chain-extending.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

GENERAL DESCRIPTION

These objects are accomplished according to the present invention through the creation of multiaziridines which can be represented by the following general formula:

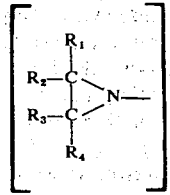

wherein
R$_1$, R$_2$, R$_3$ and R$_4$ are monovalent radicals that may be the same or different selected from the group hydrogen, 1 to 5 carbon alkyl and 1 to 5 carbon alkenyl,
R$_5$ is a multivalent hydrocarbon radical containing 2 to 24 carbon atoms, and
n is an integer from 2 to 4.

The objects of the invention are further accomplished by production of improved polymer products through reaction of a carboxyl containing compound with a multiaziridine as represented by the foregoing formula. Advantageously, the multiaziridine will be present in about 1 to 10% by weight of the reaction mixture and preferably 1 to 10 parts of the multiaziridine will be used for each 100 parts of the carboxyl containing polymer.

Within the class of multiaziridines as represented by the foregoing formula, it has been found that particularly good results in curing of carboxyl containing polymers are obtained from the use of two specific groups of multiaziridines, namely, compounds having the formula:

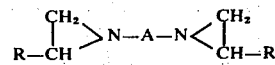

wherein
A is a 4 to 6 carbon atom saturated or unsaturated aliphatic radical, and
R is hydrogen or 1 to 3 carbon atom alkyl.
And compounds having the formula:

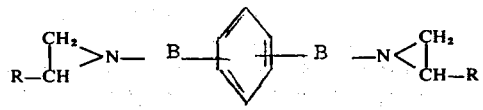

wherein
R is hydrogen or 1 to 3 carbon alkyl, and
B is an alkylene radical containing 1 to 6 carbon atoms.

It has been found that the curing of carboxyl containing polymers in accordance with the invention produces usually fine results with carboxyl terminated polymers and particularly carboxyl terminated polyolefins, e.g., dicarboxyl polybutadiene. The resulting di-olefin polymers may be hydrogenated to reduce unsaturation and may include copolymers with styrene and other copolymerizable monomers. The processes of the invention may also be used to cure copolymers, terpolymers, and the like of acrylic acid or methacrylic acid with butadiene, isoprene, acrylonitrile, styrene, methyl methacrylate, butyl acrylate and so forth. Carboxyl containing copolymers of maleic anhydride and other copolymerizable vinyl monomers can also be used as well as carboxyl terminated polyesters prepared by the condensation of an excess of a di, tri and poly-carboxylic acid and a minor amount of a diol, triol or other polyol (glycol, glycerol, pentaerythritol, etc.) and mixtures thereof.

Success of the present invention is due in part to the discovery that multiaziridines as hereinbefore defined cure carboxyl containing polymers in a fashion which produces a unique combination of properties, specifically, improved elastomeric characteristics in combination with a hardness and gel content which renders the cured polymers particularly useful for gaskets, seals, potting compounds, metal coatings, films, rub backings and rocket binders. In the case of dicarboxyl polybutadiene, curing procedures of the invention produce soft rubber with a unique combination of gel content, hardness and plasticity.

The success of the invention is further due, in part, to the discovery that controlled properties, e.g., plasticity, burning rate, and hardness, may be controlled in the curing of polycarboxy polymers by using a combination of multiaziridines chosen so that one of the multiaziridines in the mixture has a high reactivity toward chain extension without much tendency toward cross-linking of the polymer and another multiaziridine in the mixture has a high reactivity toward cross-linking of the polymer without much tendency toward chain-extending. It has been found that the greater the substitution of the aziridino groups in such compounds with alkyl group, the greater the tendency toward chain-extending as opposed to cross-linking and vice versa.

EXAMPLES

A more complete understanding of the new methods and products of this invention may be had by reference to the following report of conditions and data from operations performed in accordance with the invention. In these examples and throughout the remaining specification and claims, all parts and percentages are by weight and all temperatures are in degrees centigrade unless otherwise specified.

EXAMPLE 1 p-bis-(N-butyleneiminomethyl)benzene

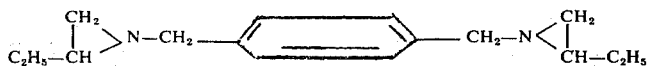

A spherical reaction vessel equipped with internal stirrer, reflex condenser, and thermometer was charged with 71 parts of pure butyleneimine, 365 parts of triethylamine, and 83 parts of $\alpha,\alpha'$-dibromo-p-xylene with stirring. After several minutes the mixture became turbid and the temperature rose to 75°C. At this point, the vessel was cooled with ice. After stirring for 10 minutes, the temperature returned back to 33°C. and a precipitate formed. This was removed by filtration after standing for 1 day. The precipitate was found to be triethylamine hydrobromide.

To the filtrate there was added 7.5 parts NaOH pellets with agitation and the solution was again filtered. Next, the filtrate was flash-distilled at 0.2 mm up to a pot temperature of 170°C. The resulting distillate was fractionated. The recovered product boiled at 110°–115°C. (0.1 mm) and amounted to 45 parts. By standard analytical procedure, the aziridine content of the product was 33.7% (calc. 34.40) and the nitrogen content was 11.77% (calc. 11.23).

EXAMPLE 2

The same compound, p-bis-(N-butyleneiminomethyl) benzene, was prepared by a procedure similar to Example 1, using $\alpha,\alpha'$-dichloro-p-xylene as a starting material and the same equipment. The vessel was charged with 71 parts pure butyleneimine, 365 parts of triethylamine, 170 parts of $\alpha,\alpha'$-dichloro-p-xylene and the contents were heated to 60°C. for 4 hours with agitation.

After filtering the solid and shaking the filtrate with about 10 pt. of NaOH pellets and filtering again, the resulting liquid was fractionated from 30 parts NaOH pellets through a column packed with glass helices.

The main fraction, which was the expected compound, boiled at 135°C. (0.5 mm) and the yield amounted to 41 parts.

| Analysis: | Aziridine: | Found: 31.98% | Calc. 34.4% |
|---|---|---|---|
| | Nitrogen: | Found: 11.93% | Calc. 11.2% |

EXAMPLE 3 p-bis-(N-ethyleneiminomethyl)benzene

A vessel as used in Example 1 was charged with 52 parts $\alpha,\alpha'$-dibromo-p-xylene, 22 parts of ethyleneimine and 365 parts triethylamine while agitating. The temperature rose to 53°C. at which point cooling was applied. The contents were stirred overnight, the precipitated triethylamine hydrobromide filtered off and the filtrate shaken with 10 parts NaOH pellets. The liquid was decanted and distilled from 20 parts NaOH pellets through a Vigreux column up to a boiling point of 87°C. The remaining material was fractionated in vacuum and the main fraction collected at 103°–110°C. (0.1 mm), amounting to 7 parts.

| Analysis: | Aziridine: | Found: 41.0% | Calc. 44.7% |
|---|---|---|---|
| | Nitrogen: | Found: 14.7% | Calc. 14.9% |

EXAMPLE 4 o-bis-(N-butyleneiminomethyl)benzene

The vessel used in Example 1 was charged with 100 parts $\alpha,\alpha'$-dibromo-o-xylene, 365 parts triethylamine, and 71 parts of pure butyleneimine. When the temperature rose to 68°, cooling was applied to the vessel. After stirring overnight, the contents were filtered and the filtrate distilled from 20 parts NaOH pellets.

The main fraction boiled at 120°–130°C. (0.2 mm) and the yield amounted to 66 parts.

| Analysis: | Aziridine: | Found: 32.3% | Calc. 34.4% |
|---|---|---|---|
| | Nitrogen: | Found: 11.3% | Calc. 11.2% |

EXAMPLE 5 p-bis-(N-propyleneiminomethyl)benzene

A vessel as described in Example 1 was charged with 100 parts of $\alpha,\alpha'$-dibromo-p-xylene, 365 parts triethylamine and 57 parts pure propyleneimine. The temperature was kept at about 50°C. by intermittent cooling. After stirring for 3 hours, the contents were filtered and the filtrate left standing for 15 hours over 10 parts of NaOH pellets. The liquid was decanted and distilled from 20 parts NaOH pellets. The main fraction boiled at 105°–110°C. (0.1 mm) and amounted to 53 parts.

| Analysis: | Aziridine: | Found: 38.0% | Calc. 38.0% |
|---|---|---|---|
| | Nitrogen: | Found: 12.4% | Calc. 12.9% |

EXAMPLE 6

1,4-di-(N-ethylenimino)butane

In a vessel of the type referred to in Example 1, 832 parts of ethylenimine were heated to 55°C. Then 40 parts potassium metal were added in small pieces over a period of 4 hours and the mixture was refluxed for another 30 minutes. Next approximately 700 parts of excess ethylenimine were distilled off, the mixture was cooled to ambient temperature (about 25°C.), and 450 parts of anhydrous ethylene glycol-dimethyl ether were added slowly with cooling, while the temperature was held to 40°C. At this point, 86 parts of 1,4-dibromobutane were added dropwise to the stirred solution of the potassium imide complex over a period of 3 hours, while the temperature was held to 35°C. When addition was completed, the reaction mixture was refluxed for 1.5 hours with a pot temperature about 70°C.

Solid precipitate formed, was filtered out and washed with dry ether. The filtrate was distilled to 87°C. vapor temperature to remove solvents. The contents of the flask were then flash distilled under high vacuum. This distillate was redistilled through a column packed with glass helices. The fraction boiling at 123°/129° was the diaziridine and amounted to 30 parts.

| Analysis: | Aziridine: | Found: 60.15% | Calc. 60% |
|---|---|---|---|
| | Nitrogen: | Found: 20.27% | Calc. 20.3% |

EXAMPLE 7

1,5-di-(N-ethylenimino)pentane

Using the apparatus and general procedure of Example 6, 915 parts of ethylenimine were stirred and refluxed with 48 parts of potassium metal in small pieces over a period of 3.5 hours. Then the mixture was refluxed for another one-half hour.

Approximately 670 parts of excess ethylenimine were distilled off, the contents of the flask cooled to room temperature and 380 parts of ethylene glycol-dimethyl ether added to it. After 2 minutes, the reaction mixture gelled while complex formation occurred, and the temperature rose to 35°C. At this point, the gel liquefied again and the temperature rose to 49°C. By cooling the temperature was arrested at this point. After cooling back to 18°C., 92 parts of 1,5-dibromopentane were added dropwise to the potassium imide-glycol ether complex over a period of 2.5 hours. The temperature was kept between 20° and 30°C. by intermittent cooling. Thickening of the reaction mixture occurred during the addition and 70 parts of dry diethyl ether were added to reduce the viscosity. The mixture was then stirred and refluxed for 3 hours and the solvents distilled off through a Vigreux column up to a vapor temperature of 83°C. The residue was fractionated through a column packed with glass helices. The main fraction boiled at 135° to 147°C. and amounted to 42 parts.

| Analysis: | Aziridine: | Found: 58.6% | Calc. 54.6% |
|---|---|---|---|
| | Nitrogen: | Found: 21.0% | Calc. 18.2% |

EXAMPLE 8

1,4-di-(N-butylenimino)butene-2

Repeating the operation of Example 6, 71 parts of butylenimine, 365 parts of trietnylamine, and 86 parts of 1,4-dibromobutene-2 were charged into the reaction vessel, intermittently agitated and cooled to keep the temperature from rising over 50°. After standing for 24 hours, the mixture was decanted through a filter cloth into a distillation vessel. The excess butylenimine and the triethylamine were distilled out through a column packed with glass helices. The residue was then distilled in vacuum without a column. The main fraction boiled at 80° to 90° (2.4 mm) and amounted to 22 parts.

| Analysis: | Aziridine: | Found: 41.5% | Calc. 43.3% |
|---|---|---|---|
| | Nitrogen: | Found: 15.1% | Calc. 14.4% |

EXAMPLE 9

1,6-di-(N-ethylenimino)hexane

Potassium ethylenimide-ethylene glycol dimethyl ether complex (1.1 mole) was prepared by the general method described in Example 6. Then, 100 parts of 1,6-dibromohexane were added dropwise with stirring over a period of 2 hours keeping the temperature from rising over 40° by cooling intermittently. During the addition, the reaction mixture was diluted with 360 parts dry diethyl ether to reduce viscosity. After stirring for 1 hour at 40°C., the temperature began to decrease and the mixture was refluxed for 3.5 hours, pot temperature being 49°C. After standing over night, the solid was filtered, washed with diethyl ether and the combined liquids distilled from 50 parts NaOH pellets through a packed column.

The solvents and excess imine were taken off as forerun and the residue was distilled through a Vigreux column. Two main fractions were obtained, the first one boiling at 121° to 135° and amounted to 33 parts.

Analysis: Aziridine: Found: 50.6% Calc. 50.0%

The second fraction boiled at 135° to 150°C. and amounted to 32 parts.

Analysis: Aziridine: Found: 54.5% Calc. 50.5%

EXAMPLE 10

A mixture was formed from 1470 parts of dicarboxyl polybutadiene (carboxyl content 0.414 milliequivalents per gram) and 57 parts of p-bis-(N-ethyleneiminomethyl) benzene. This mixture was poured into small polyethylene molds and small polystyrene molds. After 4 days in an oven at 80°C., the following physical properties were found for the resulting rubbery polymer.

| Shore 00 hardness: | 68 |
|---|---|
| Williams plasticity: | 210 |
| Gel percent: | 80. |

EXAMPLE 11

A mixture was formed of 2314 parts of dicarboxy polybutadiene and 117 parts of o-bis-(N-butyleneiminomethyl)benzene. The mixture was then cast and cured as described in Example 10. The physical properties of the rubbery polymer formed were as follows:

| | |
|---|---|
| Shore 00 hardness: | 38 |
| Gel percent: | 60. |

EXAMPLE 12

A mixture was formed from 2490 parts of dicarboxy polybutadiene and 117 parts of p-bis-(N-propyleneiminomethyl) benzene. The mixture was then cast and cured as noted in Example 10. The resulting polymer molded products were then tested according to standard test method and found to have the following properties:

| | |
|---|---|
| Shore 00 hardness: | 27 |
| Williams plasticity: | 79 |
| Gel percent: | 54. |

EXAMPLE 13

A mixture was formed from the following ingredients:
  dicarboxy terminated polybutadiene — 1574 parts
  p-(bis-N-ethyleneiminomethyl) benzene — 54 parts
  p(bis-N-butyleneiminomethyl) benzene — 20 parts.

The mixture was cast into test shape molds and cured 4 days at 80°C. Tests performed on the resulting elastomeric products give the following properties:

| | |
|---|---|
| Shore 00 hardness: | 76 |
| Williams plasticity: | 285. |

EXAMPLE 14

A mixture was made from 1477 parts of dicarboxyl polybutadiene and 43 parts of 1,4-di-(N-ethylenimino)butane. The mixture was cast in suitable test shape molds and cured for 4 days at 80°C. A soft rubber was obtained with a gel content of 23%.

EXAMPLE 15

The procedure of Example 14 was repeated using a mixture of 1510 parts of dicarboxy polybutadiene and 48 parts of 1,5-di-(N-ethyleneimino) pentane. A soft rubber was obtained having a gel content of 37%.

EXAMPLE 16

A mixture was prepared from 1974 parts of dicarboxy polybutadiene and 79 parts of 1,4-di-(N-butylenimino)butene-2. The mixture was cast into test sample mold and cured for 15 minutes at 160°C. The resulting rubbery polymer had a Shore 00 hardness of 20 and a gel content of 50%.

EXAMPLE 17

1,5-di-(N-ethyleneimino)-3-(N-ethyleniminomethyl)-pentane

The general procedure of Example 6 was repeated to form about 200 parts of potassium imide complexed with anhydrous ethylene glycol-dimethyl ether. To this was then added dropwise, with the termperature maintained at 35°C., 80 parts of 1,5-dibromo-3-bromomethyl pentane. When the addition was completed, the reaction mixture was refluxed for 2 hours at about 70°C. A solid precipitate formed and was recovered by filtration, freed of solvents and recovered in final form by vacuum distillation was the main product.

EXAMPLE 18

In a suitable mold, 1441 parts of a carboxylated polybutadiene having a molecular weight of from 5000 to 5500 were mixed with 60.9 parts of meta-bis-(N-ethyleniminoethyl) benzene to form a homogeneous mixture. The mixture was placed in an oven at 80°C. for 3 days. A rubbery polymer was obtained which gave the following data:

| | |
|---|---|
| Shore 00 Hardness: | 63 |
| Plasticity (Williams): | 182 |
| Gel Content, % | 82. |

EXAMPLE 19

Dicarboxy-polybutadiene 3078 parts, (11.58 milliequivalent of acid) with an approximate molecular weight of 5500 was mixed as in Example 18 with 147 parts of a previously prepared mixture consisting of 1260 parts meta-bis-(N-ethyleniminoethyl) benzene and 210 parts meta-bis-(N-butyleniminoethyl) benzene. After being kept in an oven of 80°C. for 3 days, a rubbery polymer was obtained which had the following physical properties:

| | |
|---|---|
| Shore 00 Hardness: | 79 |
| Plasticity (Williams): | 210 |
| Gel Content, % | 85. |

EXAMPLE 20

Dicarboxy-polybutandiene (0.3166 milliequivalent of acid per gram), 1608 parts were mixed with 47 parts of meta-bis-(N-ethyleniminoethyl) benzene and 17 parts meta-bis-(N-butyleniminoethyl) benzene and placed in an oven 4 days at 80°C. A rubbery polymer was obtained which had the following physical properties:

| | |
|---|---|
| Shore 00 Hardness: | 85 |
| Plasticity (Williams): | 265 |
| Gel Content, % | 94. |

EXAMPLE 21

This example shows that the physical properties of the resulting rubbery polymers were better when the meta-bis-(N-ethyleniminoethyl) aromatic compound was used in excess. The following three experiments demonstrate this observation. The following mixtures of parts as listed:

| Dicarboxy-Polybutadiene | Equivalent Acid | Meta-bis-(N-ethylenimino-ethyl) benzene | Equivalent Aziridine | % Excess Aziridine |
|---|---|---|---|---|
| A | 21.57 | 0.01 | 1.08 | 0.01 | 0 |
| B | 21.57 | 0.01 | 1.24 | 0.0115 | 15 |
| C | 21.57 | 0.01 | 1.405 | 0.013 | 30 | were placed in an oven at 35°C. for 4 days using previously described molds as containers for the liquid prepolymer mixtures. The resulting rubbery polymer had the following physical properties:

| | Shore 00 Hardness | Plasticity (Williams) | % Gel |
|---|---|---|---|
| A | 19 | 95 | 66 |
| B | 83 | 278 | 94 |
| C | 84 | 281 | 93 |

EXAMPLE 22

The polyester used for Examples 22, 23 and 24 was prepared from 19 parts of ethylene glycol, 11 parts of diethylene glycol and 69 parts of adipic acid. It had 1.247 milli-equivalent of acid per gram.

This carboxy-terminated polyester, 2708 parts were mixed with 379 parts of meta-bis-(N-ethyleniminoethyl) benzene and placed in an oven for 4 days at 40°C. using molds as described before. A rubbery polymer was obtained.

EXAMPLE 23

The polyester of Example 22 (400 parts) was mixed with 66.1 parts meta-bis-(N-ethyleniminoethyl) benzene (16% excess) and kept in an oven at 80°C. for 4 days to yield a rubbery polymer. The physical properties of the rubbery polymer were:

| Shore 00 Hardness: | 82 |
|---|---|
| Plasticity (Williams): | 205 |
| Gel Content, % | 88. |

EXAMPLE 24

The carboxy-terminated polyester of Example 22, 11468 parts, was mixed with 2007 parts of meta-bis-(N-propyleniminoethyl) benzene (15% excess) and kept in an oven at 80°C. for days to yield a rubbery polymer.

The properties of the rubbery polymer were:

| Shore 00 Hardness: | 84 |
|---|---|
| Plasticity (Williams): | 209 |
| Gel Content, % | 93. |

EXAMPLE 25

For this example, the polycarboxyl compound used was "Emery Dimer Acid 3079-S". It consists largely of a dimerized polyunsaturated acid, such as linoleic acid, having a neutralization equivalent of 292/298, dimer acid content of 95%, trimer acid content of 4%, and about 1.5% of monomeric acid.

"Emery Dimer Acid 3079-S", 28 parts, and 10.8 parts of meta-bis-(N-ethyleniminoethyl) benzene were thoroughly mixed in an aluminum mold. After standing at room temperature for 10 minutes, a rubbery cross-linked polymer was obtained with a Shore A hardness of 40.

EXAMPLE 26

A dicarboxyl polybutadiene, 1782 parts (6.077 milli-equivalent of acid), was mixed in a polystyrene mold with 89 parts of meta-bis-(N-ethyleniminoisopropyl) benzene

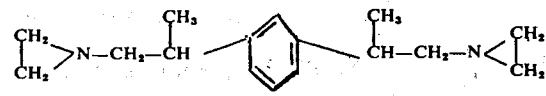

and cured for 5 days at 80°.

Physical properties of the resulting rubbery polymer:

| Shore 00 Hardness: | 84 |
|---|---|
| Plasticity (Williams): | 259 |
| Gel Content, % | 93 |

EXAMPLE 27

To 1802 parts of a polyester with carboxyl end groups as described in Example 22, there was mixed 384 parts of meta-bis-(N-ethyleniminoisopropyl) benzene and cured 4 days at 80°C., to yield a rubbery polymer.

The physical properties of the rubbery polymer were:

| Shore 00 Hardness: | 84 |
|---|---|
| Plasticity (Williams): | 216 |
| Gel Content, % | 89. |

EXAMPLE 28

In this operation, a dicarboxylpolybutadine with 0.3693 milliequivalent of acid per gram was used in conjunction with varying amounts of meta-bis-(N-ethyleniminoethyl) benzene. The experimental conditions were as described in Example 21.

The results were as listed below for mixtures formed of parts as indicated:

| Dicarboxyl-polybutadiene | Meta-bis-(N-ethyl-eniminoethyl) benzene | % Excess Aziridine |
|---|---|---|
| 1445 | 58 | 0 |
| 1523 | 64 | 5 |
| 1740 | 76 | 10 |

-continued

| | | |
|---|---|---|
| 1493 | 69 | 15 |

Properties of Rubber Obtained

| Shore 00 Hardness | Plasticity (Williams) | % Gel |
|---|---|---|
| 35 | 112 | 67 |
| 45 | 124 | 72 |
| 48 | 129 | 70 |
| 51 | 127 | 71 |

EXAMPLE 29

The following procedure was used to prepare a test rocket for showing the effectiveness of the compositions of this invention as a propellant binder. There was mixed with 2092 parts of a carboxy-terminated polybutadiene having an acid titer of 0.3762 milliequivalents per gram, 64 parts of meta-bis-(N-ethyleniminoethyl) benzene and 31 parts of meta-bis-(N-butyleniminoethyl) benzene.

One hundred eleven parts of ammonium perchlorate were added to 152 parts of the above mixture together with one drop of plasticizer in a mortar and ground to a homogeneous paste.

This paste was tamped into copper tubing closed at one end, care being taken to avoid air entrapment. A hole was made in the charge by inserting a steel mandrel and the copper tubing and contents heated to 80°C. for 3 days, at which time the pasty material became very hard. The mandrel was then removed and the rocket thus formed was test fired and proved successful.

EXAMPLE 30

A carboxy-terminated polybutadine (1790 parts) having an acid titer of 0.3762 milliequivalents per gram was mixed with 63 parts of meta-bis-(N-ethyleniminoethyl) benzene and 23 parts of meta-bis-(N-butyleniminoethyl) benzene. Ammonium chlorate (1540 parts) was added to 210 parts of the above mixture in a mortar and mixed in accordance with the procedure set forth in Example 29 and the propellant composition placed in the copper tubing and cured as set forth in Example 29. The rocket was test fired and showed the effectiveness of the composition of this invention as a binder in a solid rocket propellant.

DISCUSSION OF DETAILS

The gel content of the polymers in the examples was determined as follows:

A 0.3 gram sample of the polymer was cut into pieces approximately 1 $mm_3$. The sample is weighed to the nearest 1/10 milligram and placed in a flask. Reagent grade benzene (100 milliliters) is pipetted into the flask and the flask tightly stoppered. The flask is placed in the dark for 24 hours and then removed and shaken to effect mixing. The solution is filtered through dry filter paper to remove the undissolved portions. An aliquot of the filtrate is then taken and evaporated to dryness and dried to a constant weight in an 80°C. vacuum oven. The percent gel is calculated as the original weight of the sample minus the weight of the residue times 100 divided by the original weight of the sample.

In making the above calculation, it must be remembered that proper consideration must be given to the fact that an aliquot is used to determine the residue.

The plasticity was determined by a test in which a small plug of cured rubber is cut to weigh approximately 1 gram in such a manner as to keep the surface as flat as possible. The sample is then placed between two sheets of paper and inserted into a Williams plastometer. The top plate is lowered quickly on the sample until contact is made. The plate is then lowered slightly and carefully while the sample is being compressed. After 3 minutes, the dial is read.

The new multiaziridino hydrocarbon compounds of the invention have been found to be unique in their action in curing carboxyl containing polymers. Of these new compounds, those containing at least three aziridino groups and those containing olefinic unsaturation in the bridging hydrocarbon group are particularly interesting.

Specific examples of multiaziridino alkanes or alkenes within the scope of the invention include:

1,4-di-(N-ethylenimino)butane
1,5-di-(N-ethylenimino)pentane
1,4-di-(N-butylenimino)butene-2
1,6-di-(N-ethylenimino)hexane
1,5-di-(N-ethylenimino)-3-(N-ethyleniminomethyl)-pentane
3-methylene-1,5-di-(N-ethylenimino)pentane
1,5-di-(N-ethylenimino)pentadiene-1,4
1,4-di-(2-methyl, 3-amylaziridino)butane With respect to multiaziridino methylene benzenes, examples of compounds encompassed by the invention include:

p-bis-(N-butyleniminomethyl)benzene
p-bis-(N-ethyleniminomethyl)benzene
o-bis-(N-butyleniminomethyl)benzene
p-bis-(N-propyleniminomethyl)benzene
p-bis-(2,3-dimethylaziridinomethyl)benzene
m-bis-(2-methyl, 3-amylaziridinomethyl)benzene
1,2,4-tris-(N-butyleniminomethyl)benzene
1,3-bis-(N-butyleniminomethyl)naphthalene
1,2,4,6-tetra-(N-ethyleniminomethyl)benzene
1,2,8-tris-(N-propyleniminomethyl)naphthalene.

Illustrative of additional multiaziridinyl aryl compounds which can be employed in producing the compositions of this invention are, for example: ortho, meta or para bis-(N-ethyleniminoethyl)benzene; ortho, meta or para bis-(N-ethyleniminoisopropyl)benzene; ortho, meta or para-bis (N-propyleniminoethyl)benzene; ortho, meta or para bis-(N-propyleniminoisopropyl)benzene; ortho, meta or para bis-(N-butyleniminoethyl)-benzene; ortho, meta or para bis-(N-butyleniminoisopropyl) benzene; 1, 3, 5, tris-(N-ethyleniminoethyl)-benzene; 1, 3, 5, tris-(N-ethyleniminoisopropyl)benzene; bis-(N-ethyleniminoethyl)naphthalenes; bis-(N-ethyleniminoisopropyl)naphthalenes; tris-(N-butyleniminoethyl)naphthalenes; bis- or tris-(N-ethyleniminoethyl)biphenyls; and the like.

Examples of the aromatic nuclei which $R_5$ represents are, for example, the di-, tri-, and tetra- valent groups derived from benzene, toluene, ethyl benzene, naphthalene, anthracene, diphenyl, phenanthrene, terphenyl, xylene and their alkyl substituted derivatives and the like. It is understood, of course, that alkyl substituted aromatic compounds such as mesitylene (trimethyl benzene) could only be a di- or tri- valent group, and durene (tetramethyl benzene) could only be divalent.

Various methods are contemplated for use in preparing aziridines of the foregoing type including any general methods for the preparation of multiaziridines now known or hereinafter developed. As an example of one method, multiaziridines may be prepared by reaction of compounds containing olefinic unsaturation with ethyleneimine or its alkyl substituted counterparts. A preferred method of preparing the new aziridino compounds is reaction of ethyleneimine with a halogenated hydrocarbon as illustrated in the foregoing examples.

In place of ethyleneimine, one can use

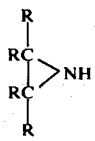

where R is hydrogen or a lower (1–5 carbon atoms) alkyl or alkenyl group (methyl, propyl, allyl, crotyl, etc.). As an example of halogenalkane, there is 1,4-dibromobutane, but one can use a compound such as [ $R' + X_n$ where $R'$ is a branched or linear aliphatic hydrocarbon chain, has from 2 to 16 carbon atoms and can be saturated or ethylenically unsaturated, X is halogen and n is a number from 2 to 6, preferably from 2 to 3.

For preparation of the aziridino aromatic compounds, bis-chloromethyl benzene may advantageously be used. However, one can use a compound such as

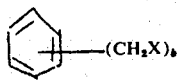

where S is halogen and b is a number from 2 to 3 and the substituent may be on any position of the aromatic ring. Monocyclic compounds are preferred, but use of polycyclic compounds is comtemplated, i.e., corresponding compounds in which the benzene group is replaced by naphthalene, anthracene, bi-phenyl, terphenyl, diphenyl-methane, -ethane, etc., triphenyl-methane, etc. The H on the aromatic nuclei can be partially or entirely replaced with lower (C1–C5) alkyl groups.

In the formation of elastomeric compositions or other reaction mixtures, between multiaziridines and carboxyl containing polymers in accordance with the invention, various reaction conditions may be employed. These will depend, to some extent, upon the particular polymers which are cured with the multiaziridines and additional compounding or modifying agents which might be incorporated in the compositions. Advantageously, the curing reaction is conducted at a temperature between 25° and 175°C. for between 0.25 and 96 hours, generally shorter times being employed the higher the temperature. A temperature range of 35° to 80°C. is preferred for making rocket propellants. A preferred range of curing times and temperatures is 15–60 minutes at 135°–165°C. for molded rubber products. Usually the curing operation will take place while the multiaziridine/polymer mixture is being suitably shaped, e.g., cast in molds, extruded through dies, calendered or cast into films or the like.

In producing the compositions of this invention, it is preferred that the amount of the multiaziridinyl hydrocarbon compound employed be such that there is at least one aziridinyl group present for each carboxyl group present in the polycarboxy organic compound employed and even more preferable that an excess of the multiaziridinyl compound over that necessary to react with the polycarboxylic organic compound be employed. By way of illustration as to what is meant in the previous statement, for each carboxyl group (COOH) in the polycarboxy compound, it is preferred to employ sufficient multiaziridinyl compound so that there is slightly more than one aziridinyl group. Useable products can be formed by mixtures which consist solely of the multiaziridine and the carboxyl containing polymer. Mixtures of two or more of either or both of these basic reactants may be employed. Also, additional compounding agents commonly employed in rubber and polymer fabrication may be incorporated. Such added materials which may typically constitute 1–75% and preferably 5–50% of the total composition including the multiaziridine and the carboxyl containing polymer. Examples of such additional materials include fillers or pigments, e.g., carbon black, chalk, zinc oxide, barium sulfate, titanium dioxide, chromium oxide and the like; fire retardants, e.g., polychloroaromatic compounds, zinc borate, antimony sulfides and the like; light stabilizers; antioxidants; plasticizers, e.g., dialkyl phthalates, fatty acid esters, etc; heat stabilizers, mold release lubricants and the like.

Oxidants which are applicable in the practice of preparing solid rocket propellants of the invention are those oxygen-containing solids which are employed as oxidizing agents and/or which readily give up oxygen. They include ammonium nitrate and other ammonium and alkali metal compounds such as potassium and sodium perchlorates, chlorates, chlorites, and hypochlorites. Dichromates, chromates, chromites, and persulfates are also applicable. Although ammonium, potassium and sodium salts are preferred, salts of other metals such as lithium, calcium, strontium, barium, magnesium, aluminum, boron, and the like, can also be used. The oxidants which are preferred are ammonium nitrate and potassium, sodium and ammonium perchlorates. In the preparation of the solid rocket propellant compositions, the oxidants are powdered to sizes preferably finer than about 200 mesh. The amount of solid oxidant employed is usually a major amount of the total composition and is generally in the range between 50 and 90 percent by weight of the total mixture. If, desired, however, less than 50 percent by weight of the oxidant can be used.

Commonly used combustion rate catalyst are metal ferrocyanides and ferricyanides. Ferric ferrocyanides such as Prussian, Berlin, Hamburg, Chinese, Paris, and Milori blue, soluble Berlin or Prussian blue which contains potassium ferric ferrocyanide, and ferric ferrocyanide which has been treated with ammonia, are among the materials which can be used. Ferrous ferricyanide or Turnbull's blue is also applicable. Other metal compounds such as nickel and copper ferrocyanides can also be employed.

The amount of burning rate catalysts used in the propellant compositions will usually be in the range from 1 to 60 parts per 100 parts of rubbery polymer with from 5 to 50 parts being most frequently preferred.

The compositions are cured at temperatures generally in the range between 25° and 175°C. The curing temperature employed is determined, at least in part, by the solid oxidant used. For example, when a nitrate such as ammonium nitrate is used as the oxidant, curing is generally effected at lower temperature than when the oxidant is ammonium perchlorate. The curing agent of this invention is particularly effective at the lower temperatures. As an illustration, excellent curing rates are obtained at temperatures between 35° and 80°C. when ammonium nitrate is used as the oxidant and when a mixture of bis-(N-ethyleniminoethyl) benzene and bis-(N-butyleniminoethyl) benzene is employed as the curative agent. Curing at these relatively low temperatures has certain advantages. The safety factor is important and obviously the hazards are less when operating at low temperatures. Another advantage is that there is no phase change in ammonium nitrate below these temperatures and, therefore, there is less tendency for cracking of the composition to occur during the curing process.

The carboxy containing polymers which are especially useful in producing the solid propellants of this invention comprise carboxy containing polymers produced from a number of starting materials. These starting materials include conjugated dienes containing from 4 to 8 carbon atoms, such as, for example, piperylene, isoprene, 1,3-hexadiene, butadiene, methylpentadiene, 1,3-octadiene, 3,4-dimethyl hexadiene-1,3, chloroprene, fluoroprene, and the like.

The carboxy containing polymers also include copolymers of the above dienes with other olefin monomers, such as, for example, styrene and alkyl styrenes, vinyl naphthalene, vinyl toluene, and the like; olefinically unsaturated heterocyclic nitrogen compounds such as, 2-vinylpyridine, 3-vinylpyridine, 4-vinylpyridine, 3,5-diethyl-4-vinylpyridine, 3-ethyl-5-vinylpyridine, 2-methyl-5-vinylpyridine, and the like and di-substituted alkenyl pyridines, quinolines, and the like; the acrylic acids and their esters, such as methylcrylic acid, acrylic acid, maleic acid, methyl methacrylate, ethyl methacrylate, propyl methacrylate, butyl methacrylate and the like; methyl vinyl ether, vinyl chloride, vinylfuran, vinylcarbazole and the like.

The above dienes and the olefic monomers can be polymerized or copolymerized by a free radical mechanism to yield carboxy containing polymers when one of the monomeric substitutes are acrylic acid or maleic acid, and the like.

The carboxy containing polymers can also be prepared by reacting di-alkali organo compounds with dienes such as butadiene and subsequently with carbon dioxide to yield carboxy terminated polymers such as carboxy terminated polybutadiene.

CONCLUSION

There has been described in sufficient detail contemplated to enable those skilled in the art to make and use the invention, new improvements in processes of curing carboxyl containing polymers. This is accomplished by the provision of multiaziridines of certain type which are themselves new and which are uniquely reactive with carboxyl containing polymers in such curing operations.

Examples of various reagents and conditions employed in producing the multiaziridines and in curing carboxyl containing polymers therewith have been given. The resulting elastomeric products possess unique combinations of hardness, gel content and plasticity rendering them particularly useful in certain indicated applications and products.

What is claimed is:

1. A method of producing a solid propellant which comprises:
    A. forming a mixture of:
        a. a solid oxidant,
        b. a polycarboxylic polymer containing at least two carboxyl groups,
        c. a multiaziridinyl hydrocarbon having the formula:

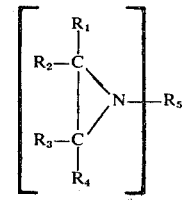

wherein
        $R_1$, $R_2$, $R_3$, $R_4$ monovalent radicals that may be the same or different selected from the group consisting of hydrogen, 1 to 5 carbon alkyl and 1 to 5 carbon alkenyl,
        $R_5$ is a multivalent olefinically unsaturated hydrocarbon radical containing 2 to 24 carbon atoms, and
        $n$ is an integer from 2 to 4, and
    B. maintaining said mixture at a temperature at which said polycarboxylic polymer and said multiaziridinyl hydrocarbon react to form a copolymeric product.

2. The method of claim 1 wherein said multiaziridinyl hydrocarbon is 1,4-di-(N-butylenimino) butene-2.

3. A method of producing a solid propellant which comprises:
    A. forming a mixture of:
        a. solid oxidant
        b. polycarboxylic polymer containing at least two carboxyl groups,
        c. multiaziridinyl hydrocarbon having the formula:

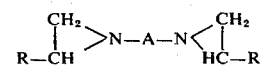

wherein
    A is 4 to 6 carbon atom olefinically unsaturated aliphatic radical and
        R is hydrogen or 1 to 3 carbon atoms alkyl radical, and
    B. maintaining said mixture at a temperature at which said polymer and said multiaziridinyl hydrocarbon react to form a copolymeric product.

4. The method of claim 3 wherein said polymer is a polycarboxylic diolefin polymer.

5. The method of claim 3 wherein said mixture additionally contains a burning rate catalyst.

6. The method of claim 3 wherein the amount of said catalyst equals 1 to 60 parts per 100 parts of said polymer.

7. The method of claim 3 wherein said temperature of step (B) is between 35° and 80°C.

8. The method of claim 3 wherein said solid oxidant constitutes between 50 and 90% by weight of said mixture.

9. The method of claim 3 wherein said multiaziridinyl hydrocarbon amounts to between 1 and 10% by weight of said mixture.

10. The method of claim 3 wherein the multiaziridinyl hydrocarbon content of said mixture is between 1 and 10 parts for each 100 parts of said polymer.

11. A solid propellant composition comprising a solid oxidizer and the copolymeric reaction product of a polycarboxylic polymer containing at least two carboxyl groups with a multiaziridinyl hydrocarbon having the formula:

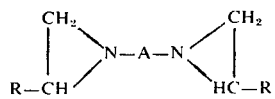

wherein A is 4 to 6 carbon atom olefinically unsaturated aliphatic radical and

R is hydrogen or 1 to 3 carbon atom alkyl radical.

12. The solid propellant composition of claim 11 wherein said solid oxidant constitutes between about 50 and 90% by weight of said mixture.

* * * * *

UNITED STATES PATENT AND TRADEMARK OFFICE
CERTIFICATE OF CORRECTION

PATENT NO. : 3,977,923
DATED : August 31, 1976
INVENTOR(S) : Heinz Uelzmann

It is certified that error appears in the above-identified patent and that said Letters Patent are hereby corrected as shown below:

Column 18, line 61, which reads: "claim 3" should read ---claim 5---.

Signed and Sealed this

Fourteenth Day of December 1976

[SEAL]

Attest:

RUTH C. MASON
Attesting Officer

C. MARSHALL DANN
Commissioner of Patents and Trademarks